United States Patent [19]
Guadagno et al.

[11] Patent Number: 5,192,501
[45] Date of Patent: Mar. 9, 1993

[54] METHOD OF FORMULATING A TEST INK FOR A FECAL OCCULT BLOOD TEST PRODUCT

[75] Inventors: Philip A. Guadagno, Vidor; Janine P. Burrows, Orange, both of Tex.

[73] Assignee: Helena Laboratories Corporation, Beaumont, Tex.

[21] Appl. No.: 333,828

[22] Filed: Apr. 4, 1989

[51] Int. Cl.$^5$ ............................................. H01N 33/50
[52] U.S. Cl. ........................................ 422/56; 436/66
[58] Field of Search ............................ 422/56; 436/66

*Primary Examiner*—Robert J. Warden
*Assistant Examiner*—Laura E. Collins
*Attorney, Agent, or Firm*—Spencer, Frank & Schneider

[57] ABSTRACT

A method of formulating a test ink for a fecal occult blood test product including the steps of: (a) providing at least one chromogen reagent in a first solution; (b) providing a moisture barrier which is a water-soluble polymer; (c) adding at least one oxygen donor reagent to the moisture barrier; (d) adding at least one color enhancer to the result of step (c) to thereby form a second solution; and (e) adding the second solution to the first solution.

19 Claims, 1 Drawing Sheet

METHOD OF FORMULATING A TEST INK FOR A FECAL OCCULT BLOOD TEST PRODUCT

CROSS-REFERENCE TO RELATED APPLICATION

This application is related to U.S. Pat. No. 5,081,040 of Patel, et al., which is owned by the assignee of this application. The aforementioned Patel, et al. applications are prior art to this application.

BACKGROUND OF THE INVENTION

The present invention relates generally to an occult blood test product, of the type to be physically placed into a toilet bowl containing a fecal specimen, for detecting the presence of fecal occult blood in an aqueous solution. More particularly, the present invention relates to an improved, reliable fecal occult blood test product which may be utilized with a minimum of human intervention. The principles of the present invention may be employed in the testing for occult blood, ferritin and myoglobin in various biological fluids.

In general terms, the testing of a fecal specimen for occult blood is based on the well-known principle that blood (more particularly hemoglobin) will function as a catalyst and cause oxygen to be liberated from an oxygen donor, with the liberated oxygen thus causing a color change in a chromogenic substance As such, the test for fecal occult blood is not only well-known, but numerous oxygen donors, numerous chromogens and numerous donor-chromogen pairs have been suggested in the prior literature. In considering the chromogens and oxygen donors which may be used, it should be appreciated that the fecal occult blood test is frequently referred to as a test for the presence of a substance having a peroxidase-like activity.

In addition, there are several principle styles of fecal occult blood test products which have been marketed or described in the literatures. These include slides, tape, wipe and throw-in-the-bowl products. Slide products require the patient to retrieve part of the stool specimen and, using a spatula or equivalent device, place part of the specimen on a paper which paper is thereafter submitted to a laboratory where a developing solution is applied to the slide. Tape products are typically utilized by a physician after a rectal examination in which instance the physician smears a stool sample on a thin, narrow tape and then a developing solution is applied to the tape. In both of these types of products, the chromogen is guaiac, and the oxygen donor or developing solution is hydrogen peroxide.

A third type of product is often referred to as the wipe type of product where a form of toilet paper is impregnated with a suitable chemical, typically the chromogen, and after a bowel movement, the patient self-wipes the anal area, and thereafter may apply the developing solution to the paper. As may be appreciated, in each of these types of products there is a need for the patient (or physician) to physically handle or physically contact the fecal specimen. Thus, there is a natural reluctance to employ these types of products, notwithstanding that they are well-known as beneficial screening agents, to assist in the early detection of colorectal cancer and other gastrointestinal disorders.

In November 1979, U.S. Pat. No. 4,175,923 issued to William Friend. This patent described a fecal occult blood test product of the throw-in-the-bowl type where a guaiac impregnated sheet was sprayed with a developing solution (hydrogen peroxide) and then placed into a toilet bowl containing a fecal specimen. If blood was present, the blood catalyzed a chromogenic reaction, and a blue color was observed in the toilet bowl. The product described in the Friend patent also included a positive monitor which would turn blue if the chemicals were functioning properly. However, the product as described in the Friend patent still required patient intervention in that the patient was required to apply the developer to the test product.

Guadagno U.S. Pat. No. 4,541,987, issued Sep. 17, 1985, relates to a throw-in-the-bowl type of product which included both positive and negative test monitors. A product generally in accordance with the teachings of the Guadagno patent has been successfully marketed by Helena Laboratories Corporation, of Beaumont, Texas, under their trademark CS-T. Helena Laboratories Corporation is the Assignee of the Guadagno patent and Assignee of the instant application. The CS-T brand of fecal occult blood test product is commercially successful and medically reliable.

In addition to the CS-T brand of fecal occult blood test product, which is in the nature of a test pad or sandwich of dry chemicals between layers of paper, a thin film type of product for throw-in-the-bowl fecal occult blood testing is known as described in the aforementioned Patel, et al. applications. However, the product of the type described in the Patel, et al. applications has not met with success in the market place even though it does not require patient intervention. The product of the Patel, et al. application does not include self-contained controls or monitors, and the product as marketed has heretofore utilized an external type of positive monitor which must be dropped into the toilet bowl.

Thus, there is a need for a less expensive, reliable, easy to use throw-in-the-bowl type of fecal occult blood test product which is easy to manufacture and provides consistent, reliable results, and which also includes built-in or self-contained positive and negative monitors. These self-contained monitors, of course, aid the patient because the monitors inform the patient if a positive or a negative result should be ignored as being induced by contaminants or being the result of loss of activity by the chromogen or oxygen donor. In this fashion, a patient will know to repeat a test rather than rely upon false test results.

Hence, the present invention responds to these needs by providing an improved formulation of film-type throw-in-the-bowl fecal occult blood type product.

SUMMARY OF THE INVENTION

The present invention provides an improved test product for the determination of the presence of occult blood, which product may be placed into a toilet bowl without patient intervention as heretofore described. The test product of the present invention includes not only a specimen test area but, in addition, a positive monitor area and a negative monitor area.

The test product is, in a preferred embodiment, a sheet of filter paper upon which the chromogen and oxygen donor are printed as a test ink. Thus, the test ink includes at least one oxygen donor reagent and at least one chromogen reagent capable of undergoing a visible color change when oxygen is liberated by the oxygen donor. The test ink may include a stabilizer for preventing premature interaction between the oxygen donor and the chromogen. The test ink is printed on the test sheet in the specimen test area and in the positive monitor are but not in the negative monitor area. A polymer barrier is then printed over the test ink. Lastly, a positive monitor ink is printed in the positive monitor area, on top of the polymer barrier. The purpose of the positive monitor ink is that if the chemicals are functioning properly, then there will be a visible color change in the positive monitor area. Thus, the positive monitor ink includes a substance which will catalyze the liberation of oxygen from the oxygen donor reagent.

BRIEF DESCRIPTION OF THE DRAWING

The foregoing objects and advantages of the present invention, together with other advantages which may be attained by the principles of the present invention, will become more apparent upon reading the following detailed description of the invention in conjunction with the drawings.

In the drawings, the single FIGURE illustrates the test product of the present invention.

DETAILED DESCRIPTION OF THE INVENTION

Figure 1:
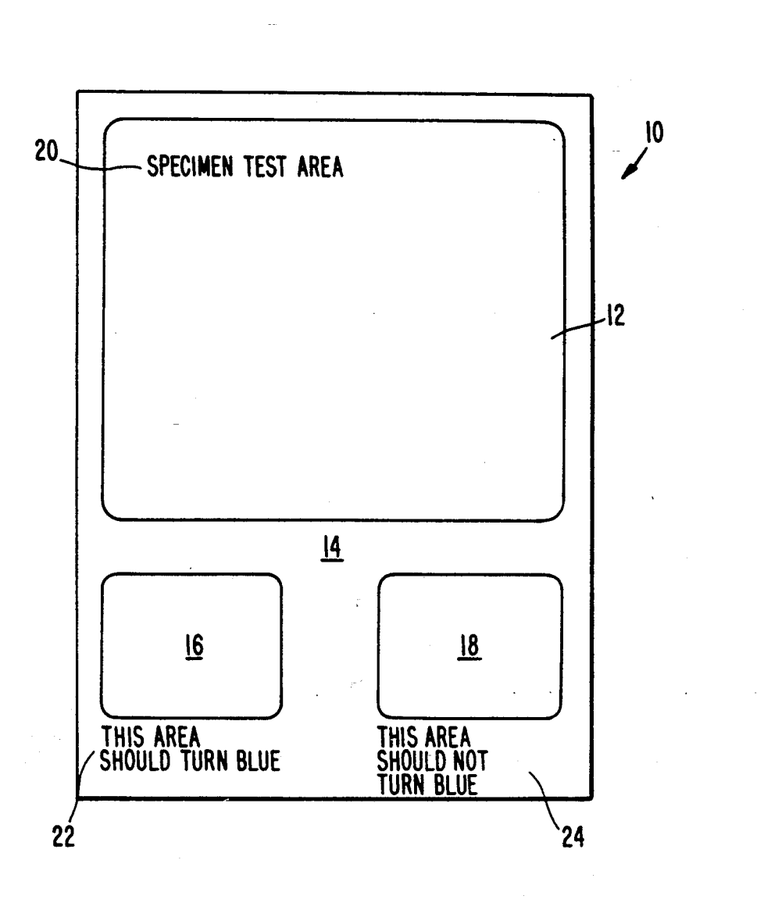

The single FIGURE illustrates a test product or test pad 10 in accordance with the present invention. The pad 10 is illustrated as a generally rectangular sheet having a large test area 12, which may advantageously occupy approximately more than half of the surface area of the sheet, and a monitor or control region 14 which may include a positive monitor test area 16 and a negative monitor test area 18. The two monitor test areas 16, 18, are approximately equal to each other in size. Suitable legends or directions 20, 22 and 24 may be included on the test product.

The entire test pad 10, in accordance with the principles of the present invention, may be a sheet of water insoluble matrix or material such as Whatman filter paper having fibers or interstitial spaces. A suitable alternative to the Whatman filter paper would be Schleicher & Schuell No. 595 filter paper. The overall dimensions of the sheet may be 4×5 inches. The paper as described is of the short fiber type which is sufficiently water repellant for the desired purpose such that the paper does not prematurely shred when initially immersed into an aqueous solution. It should be pointed out that all dimensions and ratios of the specimen test area and monitor areas are for illustrative purposes and should not be taken as a limitation on the present invention.

A test ink is deposited, i.e., printed on the entire sheet except the negative monitor test area 18. The printing deposits the test ink onto the test sheet, and the terms "printing" and "depositing" are used in the broad sense to include not only placing the ink on the surface of the sheet but also to include any desired degree of impregnation of the ink into the sheet. The test ink includes at least one chromogen reagent which will undergo a visible color change in the presence of liberated oxygen, and at least one oxygen donor reagent which will liberate oxygen when catalyzed by the presence of hemoglobin. It should be appreciated that the prior art literature lists or catalogs virtually hundreds of chromogens and virtually hundreds of oxygen donors, but the prior art does not necessarily indicate which chromogen-donor pairs or couples are suitable for detecting hemoglobin and which are printable and which may be suitably isolated as to preclude premature interaction as will be hereinafter described.

According to the principles of the present invention, we have discovered that a preferred chromogen is 3,3′,5,5′-tetramethylbenzidine and a preferred oxygen donor is cumene hydroperoxide ($\alpha,\alpha'$-dimethylbenzyl hydroperoxide).

However, it must be appreciated that it is not satisfactory to merely determine the appropriate quantities of the above two ingredients (or the appropriate quantities of all the other ingredients) necessary to achieve the desired sensitivity, mix them together and deposit them on the test sheet. This does not assure desired sensitivity nor reproducibility of results nor reliability. Thus, it is not merely satisfactory to calculate molarities and provide suitable quantities of chromogen, oxygen donor and any other ingredients for a stoichiometrically balanced reaction. Such a procedure would produce a test composition which would function properly in the laboratory, such as in a test tube, but not necessarily be mechanically printable and not necessarily be functional under normally occurring conditions. In addition, in the system described herein, the chromogen is a solid at room temperature and must be dissolved or solubilized in a solvent which will be inert or inactive relative to the detection of hemoglobin. According to the principles of the present invention, a preferred solvent or surfactant is alkylphenoxypolyethoxyethanol which is marketed as Triton X-100 by Sigma Chemical Co.

As will be further described, the positive monitor area will contain a substance having peroxidase-like the test product and thereafter until the test product is immersed in a toilet bowl, it is important to prevent the positive monitor from catalyzing a reaction between the oxygen donor and the chromogen. For this reason, it may be desirable for the test ink to include a stabilizing agent which prevents the chromogen and oxygen donor from interacting prematurely. A suitable stabilizer is triethanolamine borate, as described in U.S. Pat. No. 4,071,318. However, the stabilizer must be encapsulated and put into solution as part of the preparation of the test ink. To accomplish this objective, the triethanolamine borate is dissolved in a foaming agent such as Stepanol AM which is distributed by the Stephan Company of Northfield, Ill. Furthermore, the preferred foaming agent provides certain additional benefits such as increasing the hydrophilic nature of the test sheet.

We have further discovered that an alternative, equally satisfactory stabilizer is boron phosphate which may also be dissolved in a foaming agent. Lastly we have discovered that within the tolerances of mechanically printing the ink, and using accelerated degradation tests as described in U.S. Pat. No. 4,071,318, substantially equivalent results have been obtained without either of the above two stabilizing agents.

In addition, the test ink includes one or more water soluble polymers which encapsulate the test ink and function as a moisture barrier against ambient moisture, e.g., humidity. The moisture barrier should be solid at room temperature, and a preferred polymer is polyvinylpyrrolidone. Preferably a low molecular weight PVP may be used such as PVP 30. The PVP also tends to render the test area 12 of the sheet 10 hydrophilic, so that the test area 12 wets more readily than the unprinted negative monitor area 18.

As will be readily appreciated by those skilled in the art, the actual concentrations of the ingredients of the composition of the test ink may be varied, which will also result in varying the sensitivity of the test product 10 and the intensity of the color which develops in a positive test. Therefore, although the invention provides a distinct color reaction when as little as 1.5 to 2.0 mg of hemoglobin per 100 ml of test sample, for a particular application the sensitivity of the kit may be increased to be outside this sensitivity range.

It should be appreciated that the present invention relates to a fecal occult blood test product which is to be utilized by patients within the privacy of their homes. Thus, the results of the use of the specimen test sheet will not be interpreted by medically skilled or medically experienced personnel. For this reason, we have included yet another ingredient in the test ink, namely, a color enhancer such as 6-methoxyquinoline.

In the preparation of the test sheet, the test ink may be deposited on the sheet by various printing techniques such as using an offset press, an ink stamp pad, a flexopress, etc. Various adjustments may be made in the formulation which is hereafter described depending upon the specific printing technique employed. The formulation hereafter described is suitable for use with an offset press or a conventional ink stamp pad.

After the test ink is printed on the entire test sheet except the negative monitor area 18, then a polymer barrier is printed over the entire sheet. Thereafter, a positive monitor ink must be applied to the positive monitor test area 16. A preferred formulation for the positive monitor test ink is a 3% solution of crystalline hemoglobin in Triton X-100 which is ground on a 3 roller mill and then printed or deposited in the positive monitor area.

A test ink made according to the following example has been evaluated for sensitivity and reproducibility of results. When compared to commercially available fecal occult blood test products which have been approved by the FDA, comparable results are achieved by the following formulation.

Example of Test Ink 22.5, grams of Triton X-100;
1.0 gram of 3,3',5,5' tetramethylbenzidine;
6.0 grams of a 10% solution of triethanolamine borate in Stepanol AM, (optional) or 6.0 grams of a 10% solution of boron phosphate in Stepanol AM, (optional);
6.0 grams of Stepanol AM;
2.5 grams of a 5% solution of polyvinyl pyrrolidone-30 in Triton X-100;
10.0 grams of cumene hydroperoxide; and
1.0 gram of 6-methoxyquinoline.

Method of Formulating the Test Ink

We believe that the method of formulating the test ink, i.e., the sequence of adding the ingredients, is important for a successful fecal occult blood test product. First, the chromogen is dissolved in the Triton X-100 solvent. The stabilizer, if it is to be utilized, is prepared separately, i.e., 6.0 grams of a 10% solution of either boron phosphate or triethanolamine borate in Stepanol AM. The stabilizer is then added to the chromogen. Then, the additional Stepanol AM is added. This becomes the first portion of the test ink. Then, separately, 2.5 grams of a 5% solution of PVP-30 in Triton X-100 is prepared. To this solution the oxygen donor is added and to this combination the color enhancer is then added. This becomes the second portion of the test ink.

The second portion of the test ink is then added to the first portion of the test ink.

The method of preparing the test sheet will now be explained. The test ink is printed on the entire test sheet excluding the negative monitor test area 18. Then, a polymer barrier is printed on the test ink. The polymer barrier is 10.0 grams of a 5% solution of PVP-30 in Triton X-100. Lastly, the positive test ink formulation as described above was printed in the positive monitor test area 16 on top of the polymer barrier. The test sheet prepared according to the aforementioned formulation produced acceptable results comparable to the results obtained with FDA-approved commercially available fecal occult blood test products.

The preferred printing technique heretofore utilized is a dual head offset press. On the first pass of the sheet through the press, the first head prints the test ink and the second head prints the graphics or legends. Then the sheet is sent through the press a second time. During this second pass through the press, the first head prints the polymer barrier and the positive test ink is printed by the second head. It should be appreciated that alternate printing equipment may be used and that the foregoing explanation is merely exemplary.

It should be pointed out that while the above formulation is given as a preferred commercial example, there are, of course, ranges for each of the ingredients. The range for each ingredient may vary by + or −15% as long as there is an excess of oxygen donor. Although the amounts of ingredients may be changed, we believe that the specific sequence or order of combining the ingredients is of importance. Also, certain ingredients may be substituted for those listed in the above formulation without departing from the spirit and scope of the present invention.

A distinction should be made between the formulation of the present invention and the prior art. While the product described in the Patel, et al. application uses many of the same ingredients as described herein, there appears to be at least two significant differences. For example, the present invention utilizes about 40-60% of Triton X-100 as a bridge, or surfactant, or solubilizing agent whereas the Patel, et al. formula includes only a small percentage of that type of ingredient. In addition, whereas the present invention includes only a small amount of PVP, functioning as a moisture barrier, the PVP is the predominant ingredient, apparently constituting about 75% of the formulation of the Patel, et al. application. Thus, the mere presence of similar or identical ingredients in the prior art, without regard to their proportions and functions, may inaccurately suggest that the present formulation taken as a whole is a mere trivial variation of prior formulations.

In addition to the foregoing, we believe that the combination of foaming agent, solvent and encapsulator provides superior results insofar as stability and printability. The use of the fecal occult blood test product of the present invention will now be summarized. After the patient has completed a bowel movement, the test sheet is merely dropped into the toilet bowl. If the chromogen undergoes a color change within the specimen test area, the result of the test is considered positive for fecal occult blood. Conversely, the absence of a color change is considered as a negative result indicating the absence of fecal occult blood. The validity of the test is confirmed by a color change in the positive monitor test area and by the absence of a color change in the negative monitor test area. After the results of the test have been visually observed, the test sheet is disposed of by merely flushing the toilet bowl.

The foregoing is a complete description of a preferred embodiment of the present invention. The invention may be modified as to ingredients and amounts while taking into account the functions of the ingredients. The invention, therefore, should be limited only by the scope of the following claims.

What is claimed is:

1. A method of formulating a test ink for a fecal occult blood test product, the method comprising the steps of:
   a. dissolving at least one chromogen reagent in a solvent comprising a surfactant to provide a first solution, said surfactant being present in an amount effective to prevent premature reaction of the at least one chromogen reagent and an oxygen donor reagent, and said at least one chromogen reagent being capable of being oxidized by an oxygen donor reagent in the presence of a substance having peroxidase-like activity to provide a visible change of color;
   b. providing a second solution comprised of at least one oxygen donor reagent dissolved in a solvent comprising a surfactant, which surfactant is the same surfactant as contained in the first solution; and
   c. adding the second solution to the first solution to provide a test ink.

2. The method as defined in claim 1, further comprising the steps of:
   dissolving at least one stabilizer in a foaming agent to provide a stabilizer solution, which at least one stabilizer prevents the at least one chromogen reagent and the at least one oxygen donor reagent from interacting prematurely; and
   adding the stabilizer solution to the first solution prior to step c.

3. The method as defined in claim 1, wherein the at least one stabilizer is selected from the group consisting of triethanolamine borate and boron phosphate.

4. The method as defined in claim 2, wherein the second solution further comprises a solvent comprising water and at least one water-soluble polymer which encapsulates the test ink and functions as a moisture barrier against ambient moisture, and which is dissolved in the solvent comprising water.

5. The method as defined in claim 4, wherein the at least one water-soluble polymer is polyvinylpyrrolidone.

6. The method as defined in claim 1, wherein said surfactant is alkylphenoxypolyethoxyethanol.

7. The method as defined in claim 1, wherein the at least one chromogen reagent is 3,3',5,5'-tetramethylbenzidine.

8. The method as defined in claim 1, wherein the at least one oxygen donor reagent is cumene hydroperoxide.

9. The method as defined in claim 1, wherein the second solution further comprises a solvent comprising water and at least one water-soluble polymer which encapsulates the test ink and functions as a moisture barrier against ambient moisture, and which is dissolved in the solvent comprising water.

10. The method as defined in claim 9, wherein the at least one water-soluble polymer is polyvinylpyrrolidone.

11. The method as defined in claim 9, wherein the second solution further comprises at least one color enhancer, and the at least one water-soluble polymer is dissolved in the solvent followed by, in the order recited, addition of the at least one oxygen donor and addition of the at least one color enhancer.

12. The method as defined in claim 11, wherein the at least one color enhancer is 6-methoxyquinoline.

13. The method as defined in claim 1, wherein said surfactant is alkylphenoxypolyethoxyethanol.

14. The method as defined in claim 1, wherein the test ink has a total content of said surfactant ranging from about 40 to about 60%.

15. A method of formulating a test ink for a fecal occult blood test product, the method comprising the steps of:
   a. dissolving 3, 3', 5, 5'-tetramethylbenzidine, which is a chromogen reagent capable of being oxidized by an oxygen donor reagent in the presence of a substance having peroxidase-like activity to provide a visually observable change of color, in a solvent comprising alkylphenoxypolyethoxyethanol, which is a surfactant, to provide a first solution, said alkylphenoxypolyethoxyethanol being present in an amount effective to prevent premature reaction of the at least one chromogen reagent and the oxygen donor reagent, and said at least one chromogen reagent being capable of being oxidized by an oxygen donor reagent in the presence of a substance having peroxidase-like activity to provide a visible change of color;
   b. dissolving polyvinylpyrrolidone, which is a water-soluble polymer and functions as a moisture barrier against ambient moisture, in a solvent comprising water to provide a second solution;
   c. adding to the second solution of step b, in the order recited, cumene hydroperoxide, which is an oxygen donor reagent, and at least one color enhancer; and
   d. adding the second solution after step c to the first solution to provide a test ink.

16. The method as defined in claim 15, further comprising the steps of:
   dissolving at least one of triethanolamine borate and boron phosphate, as a stabilizing agent to prevent the chromogen reagent and the oxygen donor reagent from interacting prematurely, in a foaming agent to provide a stabilizer solution; and
   adding the stabilizer solution to the first solution prior to step d.

17. The method as defined in claim 15, wherein the at least one color enhancer is 6-methoxyquinoline.

18. The method as defined in claim 15, wherein the solvent comprising water of the second solution additionally comprises alkylphenoxypolyethoxyethanol.

19. The method as defined in claim 18, wherein the test ink has a total content of said surfactant ranging from about 40 to about 60%.

* * * * *

UNITED STATES PATENT AND TRADEMARK OFFICE
CERTIFICATE OF CORRECTION

PATENT NO. : 5,192,501           Page 1 of 5
DATED : March 9, 1993
INVENTOR(S) : Philip A. Guadagno et al It is certified that error appears in the above-indentified patent and that said Letters Patent is hereby corrected as shown below:

On the title page, insert the following item:

--[56]          References Cited

U.S. PATENT DOCUMENTS

| Number | Date | Inventor | Class |
|---|---|---|---|
| 2,223,520 | 12/1940 | Ioannu | 435/43 |
| 2,290,436 | 7/1942 | Kamlet | 436/66 |
| 2,387,244 | 10/1945 | Compton et al | 436/95 |
| 2,394,140 | 2/1946 | Biscow | 606/119 |
| 2,418,392 | 4/1947 | Bender | 206/0.5 |
| 2,567,445 | 9/1951 | Parker | 436/20 |
| 2,754,289 | 7/1956 | Meyer | 526/68 |
| 2,773,906 | 12/1956 | Emerson | 568/573 |
| 2,799,660 | 7/1957 | Nicholls et al | 436/66 |
| 2,800,457 | 7/1957 | Green et al | 428/402.2 |
| 2,800,458 | 7/1957 | Svoboda et al | 428/402.2 |
| 2,823,984 | 2/1958 | Mavrodineanu | 436/124 |
| 2,838,377 | 6/1958 | Fonner | 436/66 |
| 2,848,308 | 8/1958 | Free | 435/14 |
| 2,886,445 | 5/1959 | Rosenthal et al | 426/5 |
| 2,893,844 | 7/1959 | Cook | 435/14 |
| 2,905,594 | 9/1959 | Morris | 435/28 |
| 2,930,695 | 3/1960 | Rosner et al | 514/734 |
| 2,953,454 | 9/1960 | Berman | 430/345 |
| 2,986,453 | 5/1961 | Collins | 422/56 |
| 3,012,976 | 12/1961 | Adams, Jr. et al | 436/66 |
| 3,017,879 | 1/1962 | Sapit et al | 128/638 |
| 3,034,922 | 5/1962 | Boe et al | 162/100 |
| 3,042,496 | 7/1962 | Fancher et al | 435/14 |
| 3,043,782 | 7/1962 | Jensen | 427/213.35 |
| 3,057,723 | 10/1962 | Jeffreys et al | 430/449 |
| 3,066,081 | 11/1962 | Rorem et al | 435/14 |

UNITED STATES PATENT AND TRADEMARK OFFICE
CERTIFICATE OF CORRECTION

PATENT NO. : 5,192,501
DATED : March 9, 1993
INVENTOR(S) : Philip A. Guadagno et al It is certified that error appears in the above-indentified patent and that said Letters Patent is hereby corrected as shown below:

```
3,092,463   6/1983    Adams, Jr. et al..422/56
3,092,464   6/1983    Adams, Jr. et al..422/56
3,116,223   12/1963   Rosner et al......435/14
3,183,173   5/1965    Oakes.............435/10
3,232,710   2/1966    Rieckmann et al...435/25
3,252,762   5/1966    Adams, Jr. et al..422/56
3,290,117   12/1966   Adams, Jr. et al..422/56
3,293,683   12/1966   Wyant.............15/104.93
3,350,278   10/1967   Gretton et al.....435/14
3,406,015   10/1968   Foster............435/28
3,406,106   10/1968   Garwood et al.....204/37.1
3,411,887   11/1968   Ghiu-Choon Ku.....435/8
3,418,079   12/1968   Rey et al.........422/56
3,438,737   4/1969    Atkinson et al....436/86
3,443,903   5/1969    Haack et al.......436/169
3,447,536   6/1969    Snyder............604/38
3,453,180   7/1969    Fraser, Jr. et al.435/14
3,466,145   9/1969    Duyne.............422/103
3,472,738   10/1969   Foster............435/28
3,507,269   4/1970    Berry.............128/636
3,509,872   5/1970    Truhan............128/771
3,511,608   5/1970    Anderson..........422/56
3,526,480   9/1970    Findl et al.......422/66
3,552,925   1/1971    Fetter............436/169
3,558,435   1/1971    Rey et al.........435/14
3,598,704   8/1971    Dablgvist.........435/14
3,625,654   12/1971   Duyne.............411/102
3,627,697   12/1971   Rey et al.........436/135
3,627,698   12/1971   Rey et al.........436/135
3,630,847   12/1971   Rey et al.........435/14
3,630,957   12/1971   Rey et al.........436/66
```

UNITED STATES PATENT AND TRADEMARK OFFICE
CERTIFICATE OF CORRECTION

PATENT NO. : 5,192,501
DATED : March 9, 1993
INVENTOR(S) : Philip A. Guadagno et al It is certified that error appears in the above-indentified patent and that said Letters Patent is hereby corrected as shown below:

```
3,654,179   4/1972    Bauer.............435/28
3,654,180   4/1972    Bauer.............435/28
3,668,076   6/1972    Rey et al.........435/28
3,672,351   6/1972    Unersax et al.....128/638
3,699,005   10/1972   Foster............435/21
3,712,853   1/1973    Rittersdorf et al.435/37
3,713,772   1/1973    Tavel.............435/14
3,811,840   5/1974    Bauer et al.......436/169
3,814,668   6/1974    Blake et al.......435/14
3,847,553   11/1974   Verbeck...........422/56
3,853,468   12/1974   Haymond...........436/531
3,853,471   12/1974   Rittersdorf et al.436/66
3,853,472   12/1974   Rittersdorf et al.436/66
3,854,885   12/1974   Fromm et al.......422/86
Re 28,575   10/1975   Bauer.............36/70R
3,912,457   10/1975   Ogawa et al.......422/56
3,917,452   11/1975   Rittersdorf et al.436/66
3,964,871   6/1976    Hochstrasser......435/10
3,975,161   8/1976    Svoboda et al.....422/56
3,986,833   10/1976   Mast et al........436/66
3,996,006   12/1976   Pagano............422/50
4,005,984   2/1977    Alsop.............436/66
4,017,261   4/1977    Svoboda et al.....422/56
4,035,150   7/1977    Jaffe.............436/66
4,046,514   9/1977    Johnston et al....422/56
4,061,468   12/1977   Lange et al.......422/56
4,063,894   12/1977   Ogawa et al.......436/66
4,071,318   1/1978    Lam...............422/56
4,092,120   5/1978    Suovaniemi et al..422/56
4,148,611   4/1979    Nand et al........436/66
4,175,923   11/1979   Friend............435/7
```

UNITED STATES PATENT AND TRADEMARK OFFICE
CERTIFICATE OF CORRECTION

PATENT NO. : 5,192,501  Page 4 of 5
DATED : March 9, 1993
INVENTOR(S) : Philip A. Guadagno et al It is certified that error appears in the above-indentified patent and that said Letters Patent is hereby corrected as shown below:

```
4,219,336   8/1980    Guthlein et al....436/66
4,220,713   9/1980    Rittersdorf et al.435/14
4,251,222   2/1981    White.............436/66
4,251,223   1/1981    White.............436/66
4,260,393   4/1981    Gibson............436/66
4,269,938   5/1981    Frank.............422/56
4,277,250   7/1981    Melnick et al.....436/66
4,278,439   7/1981    White.............436/66
4,292,272   9/1981    Kitajima et al....422/57
4,303,409   12/1981   Ogawa et al.......436/93
4,310,626   1/1982    Burkhardt et al...435/28
4,329,317   5/1982    Detweiler et al...422/58
4,333,734   6/1982    Fleisher..........436/66
4,365,970   12/1982   Lawrence et al....436/66
4,385,114   5/1983    Güthlein et al....435
4,447,542   5/1984    Gantzer...........436/66
4,486,536   12/1984   Baker et al.......436/66
4,493,892   1/1985    Fleisher..........435/28
4,511,533   4/1985    Guadagno..........422/61
4,541,987   9/1985    Guadagno..........422/56
4,556,640   12/1985   Gantzer. .........435/28
4,578,358   3/1986    Oksman et al......436/66
4,725,553   2/1988    Guadagno..........436/66
4,742,002   5/1988    Guadagno et al....435/28
```

UNITED STATES PATENT AND TRADEMARK OFFICE
CERTIFICATE OF CORRECTION

PATENT NO. : 5,192,501
DATED : March 9, 1993
INVENTOR(S) : Philip A. Guadagno et al It is certified that error appears in the above-indentified patent and that said Letters Patent is hereby corrected as shown below:

```
          FOREIGN PATENT DOCUMENTS
093595    11/1983  Europe
0222700   10/1986  Europe
0124215    2/1984  Europe
0233144    1/1987  Europe
047359     2/1972  Japan
1018563    1/1966  United Kingdom
2147416A   1/1984  United Kingdom
```

Signed and Sealed this

Twentieth Day of December, 1994

Attest:

BRUCE LEHMAN

Attesting Officer     Commissioner of Patents and Trademarks